(12) United States Patent
Lin et al.

(10) Patent No.: US 10,618,859 B2
(45) Date of Patent: Apr. 14, 2020

(54) METHOD AND SYSTEM FOR REMOVAL OF OXYGEN IN OXIDATIVE DEHYDROGENATION PROCESS

(71) Applicant: DAIREN CHEMICAL CORPORATION, Taipei (TW)

(72) Inventors: Tian-Yuan Lin, Taipei (TW); Shih-Bo Hung, Taipei (TW); Yung-Kang Chao, Taipei (TW)

(73) Assignee: DAIREN CHEMICAL CORPORATION, Taipei (TW)

( * ) Notice: Subject to any disclaimer, the term of this patent is extended or adjusted under 35 U.S.C. 154(b) by 0 days.

(21) Appl. No.: 16/413,000

(22) Filed: May 15, 2019

(65) Prior Publication Data

US 2019/0284116 A1 Sep. 19, 2019

Related U.S. Application Data

(63) Continuation-in-part of application No. 15/921,310, filed on Mar. 14, 2018, now Pat. No. 10,322,985.

(51) Int. Cl.
| | |
|---|---|
| *C07C 7/148* | (2006.01) |
| *B01D 53/14* | (2006.01) |
| *C07C 7/00* | (2006.01) |
| *C07C 5/48* | (2006.01) |

(52) U.S. Cl.
CPC ............ *C07C 7/1485* (2013.01); *C07C 5/48* (2013.01); *C07C 7/005* (2013.01)

(58) Field of Classification Search
None
See application file for complete search history.

(56) References Cited

U.S. PATENT DOCUMENTS

| | | | |
|---|---|---|---|
| 2,351,167 A | 6/1944 | Ware et al. | |
| 3,361,531 A | 1/1968 | Erb et al. | |
| 3,549,719 A * | 12/1970 | Duyverman | ............ C07C 7/148 |
| | | | 423/219 |
| 3,762,133 A * | 10/1973 | Merriman | ............... B01D 53/14 |
| | | | 95/163 |
| 4,105,588 A | 8/1978 | Balducci et al. | |
| 4,299,800 A | 11/1981 | Nishikawa et al. | |
| 5,157,204 A | 10/1992 | Brown et al. | |
| 5,446,232 A * | 8/1995 | Chen | ......................... C01B 3/58 |
| | | | 423/219 |
| 6,747,066 B2 | 6/2004 | Wang et al. | |
| 7,707,837 B2 | 5/2010 | Inui et al. | |
| 8,519,210 B2 | 8/2013 | Arnold et al. | |
| 2005/0281725 A1 | 12/2005 | Hague et al. | |

(Continued)

FOREIGN PATENT DOCUMENTS

| | | |
|---|---|---|
| WO | 2004033598 A1 | 4/2004 |
| WO | 2010115108 A1 | 10/2010 |
| WO | 2015075497 A1 | 5/2015 |

*Primary Examiner* — Philip Y Louie
(74) *Attorney, Agent, or Firm* — Nixon Peabody LLP; Thomas P. Pavelko

(57) ABSTRACT

The present invention relates generally to methods and systems for removing oxygen from at least one product stream of a hydrocarbon oxidative dehydrogenation process. More specifically, in some embodiments, the oxidative dehydrogenation process is an ethane oxidative dehydrogenation process for producing ethylene, or a mixed alkane oxidative dehydrogenation process for producing ethylene and propylene, among other components.

19 Claims, 3 Drawing Sheets

(56) References Cited

U.S. PATENT DOCUMENTS

| | | |
|---|---|---|
| 2007/0299278 A1 | 12/2007 | Hechler et al. |
| 2008/0183024 A1 | 7/2008 | Klanner et al. |
| 2010/0255986 A1 | 10/2010 | Gaffney et al. |
| 2010/0256432 A1 | 10/2010 | Arnold et al. |
| 2010/0261856 A1 | 10/2010 | Esinger |
| 2014/0058151 A1 | 2/2014 | Rende et al. |
| 2014/0249339 A1* | 9/2014 | Simanzhenkov .... B01J 19/0046 585/252 |
| 2014/0316181 A1 | 10/2014 | Averlant et al. |

* cited by examiner

METHOD AND SYSTEM FOR REMOVAL OF OXYGEN IN OXIDATIVE DEHYDROGENATION PROCESS

CROSS-REFERENCE TO RELATED APPLICATIONS

This application is a Continuation-in-part ("CIP") of Non-provisional application Ser. No. 15/921,310, filed Mar. 14, 2018, entitled "METHOD AND SYSTEM FOR REMOVAL OF OXYGEN IN OXIDATIVE DEHYDROGENATION PROCESS", the entire contents of which are herein incorporated by reference.

FIELD OF THE INVENTION

The present invention relates generally to methods and systems for removing oxygen from at least one product stream of a hydrocarbon oxidative dehydrogenation process. More specifically, in some embodiments, the oxidative dehydrogenation process is an ethane oxidative dehydrogenation process for producing ethylene. In other embodiments, the oxidative dehydrogenation process is a mixed alkane oxidative dehydrogenation process.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Ethylene is a commercial and industrially important petrochemical used for the manufacture of polymers and various chemical products. One process for producing ethylene is the catalytic dehydrogenation of ethane in the presence of oxygen. This process is called oxidative dehydrogenation (ODH). In the oxidative dehydrogenation of ethane, the major component in the product is ethylene, however smaller amounts of impurities such as oxygen, carbon dioxide, and carbon monoxide are also present in the oxidative dehydrogenation product. In other embodiments, the oxidative dehydrogenation process is a mixed alkane oxidative dehydrogenation process. It is important to reduce and/or remove the amount of oxygen in the oxidative dehydrogenation product, since the oxygen can cause a number of problems during the handling of the oxidative dehydrogenation product, and/or during the recovery of the ethylene therefrom. As such there is a need in the art for methods and systems for reducing and/or removing the amount of oxygen from an oxidative dehydrogenation product and/or a product stream of an oxidative dehydrogenation process. In various embodiments, the methods and systems of the present invention meet that need.

SUMMARY OF THE INVENTION

The following embodiments and aspects thereof are described and illustrated in conjunction with systems, articles of manufacture, compositions and methods which are meant to be exemplary and illustrative, not limiting in scope.

In various embodiments, the present invention provides a method for removing oxygen from a product stream of an oxidative dehydrogenation process, comprising: contacting the product stream of the oxidative dehydrogenation process with at least one oxygen removal catalyst in at least one oxygen removal reactor, wherein the product stream has a baseline oxygen content; recovering a first effluent stream from the at least one oxygen removal reactor, wherein the first effluent stream has a first oxygen content, wherein the first oxygen content of the first effluent stream is reduced compared to the baseline oxygen content of the product stream; contacting the first effluent stream with at least one oxygen absorbent in at least one absorber unit; and recovering a second effluent stream from the at least one absorber unit, wherein the second effluent stream has a second oxygen content, wherein the second oxygen content of the second effluent stream is reduced compared to the first oxygen content of the first effluent stream. In some embodiments, the method further comprises heating the product stream before contacting the product stream with the at least one oxygen removal catalyst. In some embodiments, the heating is effected at a temperature of 100° C. to 600° C. In some embodiments, the method further comprises cooling the first effluent stream before contacting the first effluent stream with the at least one oxygen absorbent. In some embodiments, the cooling is effected at a temperature of 25° C. to 130° C. In some embodiments, the at least one oxygen removal catalyst comprises at least one metal selected from Fe, Ru, Os, Co, Rh, Ir, Ni, Pd, Pt, and Mn. In some embodiments, the at least one metal is Pd. In other embodiments, the at least one metal is Mn. In some embodiments, the at least one oxygen absorbent comprises at least one metal selected from Cu, Ag, Au, Zn, Cd, and Hg. In some embodiments, the at least one metal is Cu. In some embodiments, the at least one oxygen absorbent comprises a molecular sieve. In some embodiments, the molecular sieve is selected from a type 3A, a type 4A, and any combination thereof. In some embodiments, the product stream comprises at least one alkane, at least one alkene, oxygen, and carbon monoxide. In some embodiments, the at least one alkene is selected from $C_2$-$C_5$ alkenes. In some embodiments, the at least one alkene is ethylene. In some embodiments, the product stream comprises at least two alkanes, at least two alkenes, carbon monoxide, carbon dioxide, water and oxygen. In some embodiments the at least two alkanes comprise three alkanes. In some embodiments, the at least two alkenes are ethylene and propylene. In some embodiments, the product stream comprises ethylene and propylene, methane, ethane, propane, carbon monoxide, carbon dioxide, water and oxygen. In some embodiments where the product stream from the oxidative dehydrogenation process comprises water, it is not necessary to remove the water from the product stream before introducing the water-containing product stream into the oxygen removal reactor inlet. In the embodiments described herein, unreacted (free) hydrogen is not present in the product stream, nor is it introduced into the oxygen removal reactor inlet. Nor are other hydrocarbons introduced into the product stream or oxygen removal reactor inlet. The only hydrocarbons present (other than minor impurities formed during the oxidative dehydrogenation process) are those described herein as the components of the product stream. Other hydrocarbons present as minor impurities, if present, are present on the order of several parts per billion by volume ("ppbv"). In some embodiments, the oxygen content of the first effluent stream after contacting the product stream with the Mn-based catalyst effects more than 72.5% reduction as compared with the baseline content of the product stream. In some embodiments, the oxygen content of the first effluent stream after contacting the product stream with the Mn-based catalyst effects more than 90% reduction as compared with the baseline content of the product stream. In some embodiments, the second oxygen content of the second effluent stream is less than or equal to 500 parts per million by volume (ppmv). In some embodiments, a ratio of the second oxygen content of the second effluent stream relative to the first oxygen content of the first effluent stream is less than 15%. In some embodiments, the product stream has a baseline gas hourly space velocity (GHSV) of 100 to 12,000 $hr^{-1}$ in the at least one oxygen removal reactor. In some embodiments, the first effluent stream has a first gas hourly space velocity (GHSV) of 100 to 12,000 $hr^{-1}$ in the at least one absorber unit. In some embodiments, the heating is effected by a heater or a combination of the heater and a heat recover exchanger. In some embodiments, the cooling is effected by a cooler. In some embodiments, the at least one oxygen removal catalyst is in the form of a catalyst bed. In some embodiments, the at least one oxygen absorbent is in the form of an absorbent bed.

In various embodiments, the present invention provides an oxygen removal system for removing oxygen from a product stream of an oxidative dehydrogenation process, comprising: at least one oxygen removal reactor for preparing a first effluent stream, wherein the at least one oxygen removal reactor comprises at least one oxygen removal catalyst, an inlet for the product stream, and an outlet for the first effluent stream; a supply line for transporting the product stream of the oxidative dehydrogenation process to the at least one oxygen removal reactor, wherein the product stream has a baseline oxygen content; a heater for heating the product stream; a cooler for cooling the first effluent stream; and at least one absorber unit for preparing a second effluent stream, wherein the at least one absorber unit comprises at least one oxygen absorbent, an inlet for the first effluent stream, and an outlet for the second effluent stream; wherein the heater is connected to the supply line for transporting the product stream to the at least one oxygen removal reactor; wherein the at least one oxygen removal reactor is connected to the heater; wherein the cooler is connected to the at least one oxygen removal reactor; and wherein the at least one absorber unit is connected to the cooler.

In some embodiments, the oxygen removal system further comprises, a heat recovery exchanger for optionally heating the product stream, wherein the heat recovery exchanger is: (i) connected to the supply line for transporting the product stream of the oxidative dehydrogenation process to the at least one oxygen removal reactor; (ii) connected to the heater; (iii) connected to the at least one oxygen removal reactor; and (iv) connected to the cooler; wherein, the at least one oxygen removal reactor is connected to the heater; and wherein, the at least one absorber unit is connected to the cooler. In some embodiments, the heat recovery exchanger is for optionally heating the product stream by utilizing recoverable heat from the first effluent stream. In some embodiments, the at least one oxygen removal catalyst comprises at least one metal selected from Fe, Ru, Os, Co, Rh, Ir, Ni, Pd, Pt, and Mn. In some embodiments, the at least one oxygen absorbent comprises at least one metal selected from Cu, Ag, Au, Zn, Cd, and Hg. In some embodiments, the at least one oxygen absorbent comprises a molecular sieve. In some embodiments, the product stream comprises at least one alkane, at least one alkene, oxygen, and carbon monoxide. In some embodiments, the product stream has a baseline gas hourly space velocity (GHSV) of 100 to 12,000 $hr^{-1}$ in the at least one oxygen removal reactor. In some embodiments, the at least one oxygen removal catalyst is an Mn-based oxygen removal catalyst. In some embodiments the Mn-based oxygen removal catalyst has the formula MnOx. In some embodiments, the Mn-based oxygen removal catalyst is a mixed oxide of Mn and at least one other metal. In some embodiments, the at least one other metal in the Mn-based oxygen removal catalyst is at least one selected from the group consisting of Cu, Ce, and Al. In some embodiments the mixed oxide of Mn comprises MnOx, and at least one metal oxide from the group consisting of CuO, $CeO_2$ and $Al_2O_3$. In some embodiments, the at least one oxygen removal catalyst is in the form of a catalyst bed. In some embodiments, the at least one oxygen absorbent is in the form of an absorbent bed. In some embodiments, the heater is effected at a temperature of 100° C. to 600° C., preferably in the range of 150° C. to 250°. In some embodiments, the cooler is effected at a temperature of 25° C. to 130° C., preferably in the range of 40° C. to 50° C. In some embodiments, the at least oxygen removal catalyst comprises at least one metal selected from Pd. In some embodiments, the at least one oxygen absorbent comprises at least one metal selected from Cu. In some embodiments, the molecular sieve is selected from a type 3A, a type 4A, and any combination thereof. In some embodiments, the at least one alkene is selected from $C_2$-$C_5$ alkenes. In some embodiments, the at least one alkene is ethylene. In some embodiments, the first effluent stream has a first oxygen content. In some embodiments, the first oxygen content of the first effluent stream is reduced compared to the baseline oxygen content of the product stream. In some embodiments, the second effluent stream has a second oxygen content. In some embodiments, the second oxygen content of the second effluent stream is reduced compared to the first oxygen content of the first effluent stream. In some embodiments, the second oxygen content of the second effluent stream is less than or equal to 500 parts per million by volume (ppmv). In some embodiments, the first effluent stream has a first gas hourly space velocity (GHSV) of 100 to 12,000 $hr^{-1}$ in the at least one absorber unit.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
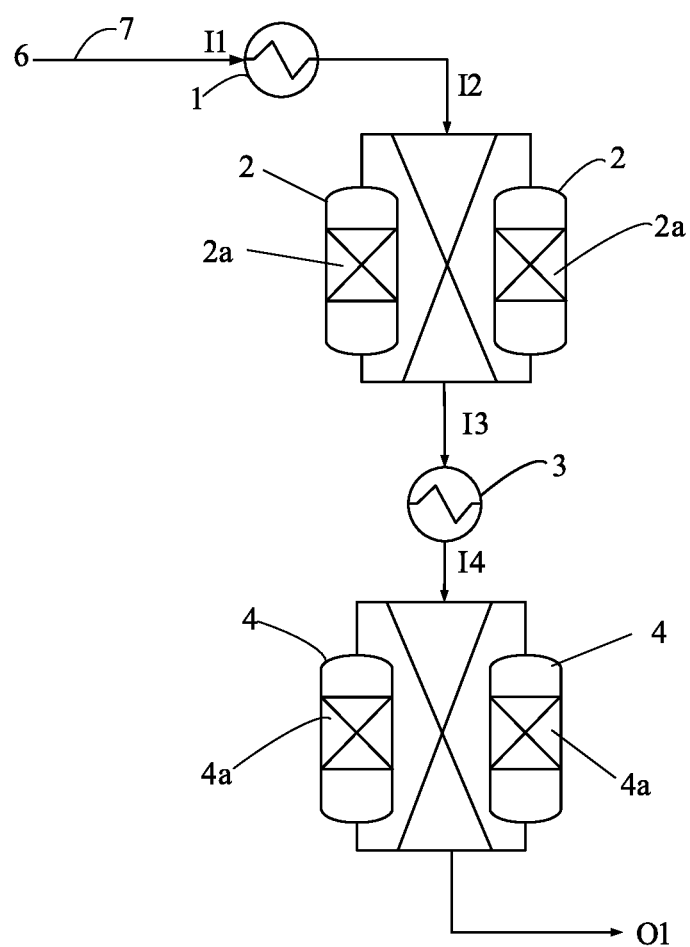
FIG. 1 depicts in accordance with various embodiments of the invention, a schematic diagram showing an embodiment of the present invention.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, systems, articles of manufacture, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the embodiments otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Optional" or "optionally" means that the subsequently described circumstance may or may not occur, so that the description includes instances where the circumstance occurs and instances where it does not.

As stated above, there is a need in the art for methods and systems for reducing and/or removing the amount of oxygen from an oxidative dehydrogenation product and/or a product stream of an oxidative dehydrogenation process. In order to meet this need, in various embodiments of the present invention we combine at least one oxygen removal reactor comprising at least one oxygen removal catalyst and recover an effluent stream from the oxygen removal reactor which has a reduced oxygen content as compared to the product stream of the oxidative dehydrogenation product. In other embodiments, we contact the effluent stream in at least one absorber unit comprising at least one oxygen absorbent.

As can be seen from the various embodiments of the invention as shown in the Examples herein, particularly for Example 1, the total oxygen removal is 91.14%. This is compared to Comparative Example 1, where the total oxygen removal is 44.00%. As can be seen from comparing Example 1 and Comparative Example 1, neither utilize an absorber unit comprising an oxygen absorbent.

Furthermore, as can be seen from the various embodiments of the invention as shown in the Examples herein, particularly for Example 2, the total oxygen removal is 99.53% when an effluent from an oxygen removal reactor is fed to an oxygen absorber unit.

Furthermore, as can be seen from the various embodiments of the invention as shown in the Examples herein, particularly for Examples 2-4, the total oxygen removal is in the range of 96.47 to 99.53%.

Figure 2:
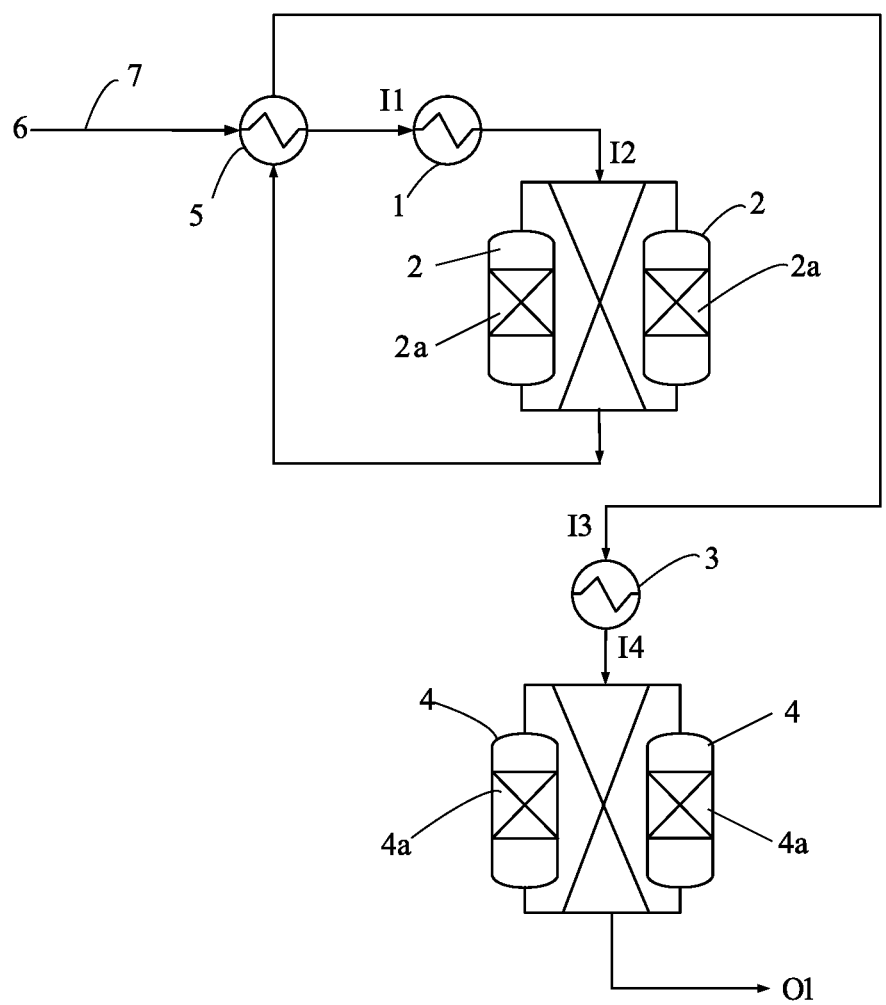
FIG. 2 depicts in accordance with various embodiments of the invention, a schematic diagram showing an embodiment of the present invention.
Figure 3:
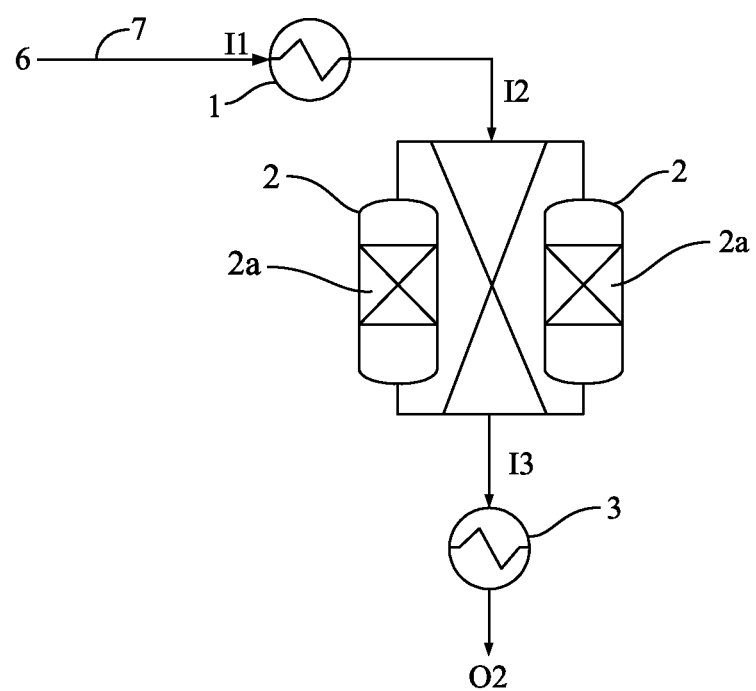
FIG. 3 depicts, in accordance with another embodiment of the invention, a schematic diagram showing an embodiment of the invention.

Referring now to FIGS. 1-3, various oxygen removal systems for removing oxygen from a product stream of an ODH process according to embodiments of the present invention are illustrated, where like numerals represent like parts.

Referring now to FIG. 1, a product stream from an oxidative dehydrogenation process 6 is fed to a heater 1 through a heater inlet I1 via a supply line 7. The heated product stream is then fed into at least one oxygen removal reactor 2 via a reactor inlet I2. The oxygen removal reactor 2 comprises a catalyst bed 2a providing for removal of at least a portion of the oxygen from the heated ODH product stream. Effluent from the oxygen removal reactor 2 is fed into a cooler 3 via a cooler inlet I3. The cooled effluent is fed into at least one absorber unit 4 via an absorber inlet I4. The absorber unit 4 comprises an absorbent or a molecular sieve bed 4a providing for removal of at least a portion of the oxygen from the cooled effluent from the oxygen removal reactor 2. Effluent from the absorber unit 4 is recovered via the absorber unit outlet O1.

Referring now to FIG. 2, a product stream from an oxidative dehydrogenation process 6 is passed through a heat recovery exchanger 5 via a supply line 7. After passing through the heat recovery exchanger 5 the product stream from the oxidative dehydrogenation process 6 is fed to a heater 1 through a heater inlet I1. The heated product stream is then fed into at least one oxygen removal reactor 2 via a reactor inlet I2. The oxygen removal reactor 2 comprises a catalyst bed 2a providing for removal of at least a portion of the oxygen from the heated ODH product stream. Effluent from the oxygen removal reactor 2 is passed through the heat recovery exchanger 5 and then into a cooler 3 via a cooler inlet I3. The cooled effluent is fed into at least one absorber unit 4 via an absorber inlet I4. The absorber unit 4 comprises an absorbent or a molecular sieve bed 4a providing for removal of at least a portion of the oxygen from the cooled effluent from the oxygen removal reactor 2. Effluent from the absorber unit 4 is recovered via the absorber unit outlet O1.

Referring to FIG. 3, a product stream from an oxidative dehydrogenation process 6 containing oxygen and at least two alkanes, at least two alkenes, carbon monoxide, carbon dioxide, and water is passed through a heater 1 through a heated inlet I1 via supply line 7. The heated product stream is then fed into at least one oxygen removal reactor 2 via a reactor inlet I2. The oxygen removal reactor 2 comprises a catalyst bed 2a providing for removal of at least a portion of the oxygen from the heated ODH product stream. Effluent from the oxygen removal reactor 2 is fed into a cooler 3 via a cooler inlet I3. By utilizing a Mn-based catalyst in catalyst bed 2a of reactor 2, the process can be performed without removing water from the incoming heated product stream, and still yield significant oxygen removal in the oxygen removal reactor 2.

Other useful flow schemes are contemplated via various embodiments of the present invention.

In various embodiments, equipment that may be used in the methods (processes) and/or systems described herein includes conventional reactors, piping, etc. The equipment is amenable and economical for use in process plants that can be either large or small.

Oxidative Dehydrogenation Product Stream

In various embodiments the systems and/or methods of the present invention comprise a supply line for transporting a product stream of an oxidative dehydrogenation process (e.g., a product stream from an oxidative dehydrogenation reactor) to an oxygen removal system and/or to at least one oxygen removal reactor (e.g., at least one oxygen removal reactor of the oxygen removal system).

In various embodiments the systems and/or methods of the present invention, a product stream of an oxidative dehydrogenation process comprises at least one alkane, at least one alkene, oxygen, and carbon monoxide. In some embodiments, the at least one alkene is selected from $C_2$-$C_5$ alkenes. In some embodiments, the at least one alkene is ethylene. In some embodiments the at least one alkane is ethane.

In some embodiments, the product stream of an oxidative dehydrogenation process further comprises carbon dioxide. In some embodiments, the product stream of an oxidative dehydrogenation process further comprises propane.

In some embodiments the oxygen present in the oxidative dehydrogenation product stream is present in a baseline amount of 1,000 ppmv to 10,000 ppmv. In some embodiments, the product stream of an oxidative dehydrogenation process has a baseline oxygen content of 1,000 ppmv to 8,000 ppmv. In some embodiments, the product stream of an oxidative dehydrogenation process has a baseline oxygen content of 1,000 ppmv to 5,000 ppmv.

In some embodiments, the product stream has a gas hourly space velocity (GHSV) of 100 to 12,000 $hr^{-1}$ in the at least one oxygen removal reactor. In some embodiments, the product stream has a gas hourly space velocity (GHSV) of 1,000 to 10,000 $hr^{-1}$ in the at least one oxygen removal reactor. In some embodiments, the product stream has a gas hourly space velocity (GHSV) of 4,000 to 9,000 $hr^{-1}$ in the at least one oxygen removal reactor.

Heater

In various embodiments the oxygen removal system of the present invention comprises a heater for heating the product stream from the oxidative dehydrogenation process. In some embodiments the heater comprises a heater inlet.

In various embodiments, the product stream is heated before being fed into the at least one oxygen removal reactor. In various embodiments, the product stream is heated before contacting the product stream with at least one oxygen removal catalyst. In some embodiments, the heating of the product stream is effected at a temperature of 100° C. to 600° C. In some embodiments, the heating of the product stream is effected at a temperature of 125° C. to 500° C. In some embodiments, the heating of the product stream is effected at a temperature of 150° C. to 400° C.

In some embodiments, the heater is connected to the supply line for transporting the product stream to the at least one oxygen removal reactor. In some embodiments, the heater is connected to the at least one oxygen removal reactor. In some embodiments, the heater is connected to and upstream from the at least one oxygen removal reactor.

Heat Recovery Exchanger

In various embodiments the oxygen removal system of the present invention further comprises a heat recovery exchanger. In some embodiments, the heat recovery exchanger may be used for optionally heating the product stream. In some embodiments, the heat recovery exchanger may be used for optionally heating the product stream by utilizing recoverable heat from the effluent stream from the oxygen removal reactors. In some embodiments, the heater and the heat recover exchanger are used for heating the product stream. In some embodiments, the heater and the heat recovery exchanger are used for heating the product stream before contacting the product stream with the at least one oxygen removal catalyst.

In some embodiments, the heating of the product stream is effected at a temperature of 80° C. to 350° C. In some embodiments, the heating of the product stream is effected at a temperature of 100° C. to 250° C. In some embodiments, the heating of the product stream is effected at a temperature of 150° C. to 200° C.

In various embodiments, the heat recovery exchanger is connected to the supply line for transporting the product stream of the oxidative dehydrogenation process to the at least one oxygen removal reactor. In some embodiments, the heat recovery exchanger is connected to the heater. In some embodiments, the heat recovery exchanger is connected to and upstream from the heater. In some embodiments, the heat recovery exchanger is connected to the at least one oxygen removal reactor. In some embodiments, the heat recovery exchanger is connected to and downstream from the at least one oxygen removal reactor. In some embodiments, the heat recovery exchanger is connected to the cooler. In some embodiments, the heat recovery exchanger is connected to and upstream from the cooler.

Oxygen Removal Reactor(s)

In various embodiments the oxygen removal system of the present invention provides at least one oxygen removal reactor for removing at least a portion of oxygen from a product stream of an oxidative dehydrogenation process, wherein the oxygen removal reactors comprise at least at least one oxygen removal catalyst. In further embodiments, the oxygen removal reactors further comprise an inlet for the product stream, and an outlet for the effluent from the oxygen removal reactors. In some embodiments, the effluent from the oxygen removal reactors is a first effluent stream from the at least one oxygen removal reactor. In some embodiments, the oxygen removal reactors comprise an oxygen removal inlet.

In various embodiments the present invention provides an oxygen removal system comprising at least one oxygen removal reactor for preparing a first effluent stream, wherein the at least one oxygen removal reactor comprise at least one oxygen removal catalyst, an inlet for the product stream, and an outlet for the first effluent stream, wherein the first effluent stream has a first oxygen content, wherein the first oxygen content of the first effluent stream is reduced compared to the baseline oxygen content of the product stream (i.e., the product stream from the oxidative dehydrogenation process).

In some embodiments, the effluent stream from the oxygen removal reactors comprises oxygen. In some embodiments, the effluent stream from the oxygen removal reactors has an oxygen content, wherein the oxygen content in the effluent stream from the oxygen removal reactors is reduced compared to the baseline oxygen content of the product stream (i.e., the product stream from the oxidative dehydrogenation process).

In some embodiments, the oxygen removal reactors, oxygen removal reaction temperature, and/or oxygen removal catalysts are at a temperature of 100° C. to 600° C. In some embodiments, the oxygen removal reactors, oxygen removal reaction temperature, and/or oxygen removal catalysts are at a temperature of 125° C. to 500° C. In some embodiments, the oxygen removal reactors, oxygen removal reaction temperature, and/or oxygen removal catalysts are at a temperature of 150° C. to 400° C.

In various embodiments the effluent stream from the oxygen removal reactors comprises oxygen, wherein the amount of oxygen in the effluent stream (i.e., the oxygen content in the effluent stream) is 100 to 5,000 parts per million by volume (ppmv). In some embodiments, the effluent stream from the oxygen removal reactors comprises oxygen, wherein the amount of oxygen in the effluent stream is 100 to 2,000 parts per million by volume (ppmv). In some embodiments, the effluent stream from the oxygen removal reactors comprises oxygen, wherein the amount of oxygen in the effluent stream is 100 to 1,000 parts per million by volume (ppmv).

In some embodiments, the effluent stream from the oxygen removal reactors has a gas hourly space velocity (GHSV) of 100 to 12,000 $hr^{-1}$, preferably 4,000 to 9,000 $hr^{-1}$. In some embodiments, the effluent stream from the oxygen removal reactors has a gas hourly space velocity (GHSV) of 1,000 to 10,000 $hr^{-1}$, preferably 4,000 to 9,000 $hr^{-1}$, and is fed into the at least one absorber unit.

In some embodiments, the effluent stream from the oxygen removal reactors has a temperature of 100° C. to 600° C. before being cooled, for example, by passing through the cooler. In some embodiments, the effluent stream from the oxygen removal reactors has a temperature of 125° C. to 500° C. In some embodiments, the effluent stream from the oxygen removal reactors has a temperature of 150° C. to 400° C. In some embodiments, the effluent stream from the oxygen removal reactor has a temperature of 150° C. to 250° C.

In various embodiments the oxygen removal system of the present invention comprises more than one oxygen removal reactor in parallel, allowing oxygen removal catalyst or an oxygen removal catalyst bed in one oxygen removal reactor to be changed while the other oxygen removal reactor is on-line, without shutting down the oxidative dehydrogenation reactor.

In various embodiments the systems and/or methods of the present invention comprise at least one oxygen removal reactor. In various embodiments the systems and/or methods of the present invention comprise at least two oxygen removal reactors.

In various embodiments, the at least one oxygen removal reactor is connected to the heater. In various embodiments, the at least one oxygen removal reactor is connected to and downstream from the heater.

Cooler

In various embodiments the oxygen removal system of the present invention comprises a cooler for cooling the effluent stream from the oxygen removal reactors. In some embodiments, the effluent stream is a first effluent stream. In various embodiments the oxygen removal system of the present invention comprises a cooler for cooling the first effluent stream from the oxygen removal reactors. In some embodiments the cooler comprises a cooler inlet.

In various embodiments the effluent stream from the oxygen removal reactors is cooled before being fed into at least one absorber unit. In some embodiments, the effluent stream is a first effluent stream. In various embodiments the effluent stream from the oxygen removal reactors is effected at a temperature of 25° C. to 130° C. In some embodiments, the cooling of the first effluent stream is effected at a temperature of 25° C. to 100° C. In some embodiments, the cooling of the first effluent stream is effected at a temperature of 25° C. to 80° C. In some embodiments, the cooling of the first effluent stream is effected at a temperature of 40° C. to 50° C.

In various embodiments, the cooler is connected to the at least one oxygen removal reactor. In various embodiments, the cooler is connected to and downstream from the at least one oxygen removal reactor.

Absorber Units

In various embodiments the oxygen removal system of the present invention comprises at least one absorber unit for removing at least a portion of oxygen from an effluent stream from at least one oxygen removal reactor, wherein the absorber units comprise at least at least one oxygen absorbent. In further embodiments, the absorber units further comprise an inlet for the effluent stream from the oxygen removal reactors, and an outlet for the effluent from the absorber units. In some embodiments, the effluent from the oxygen removal reactors is a first effluent stream. In some embodiments, the effluent stream from the absorber units is a second effluent stream. In some embodiments, the absorber units comprise an absorber unit inlet. In some embodiments the absorber units comprise an absorber unit outlet. In some embodiments, the flow in the absorber unit(s) has a gas hourly space velocity (GHSV) of 3,000 to 4,000 in the at least one absorber unit.

In various embodiments the present invention provides an oxygen removal system comprising at least one absorber unit for preparing a second effluent stream, wherein the at least one absorber unit comprise at least one oxygen absorbent, an inlet for the first effluent stream, and an outlet for the second effluent stream, wherein the second effluent stream has a second oxygen content, wherein the second oxygen content of the second effluent stream is reduced compared to the oxygen content of the first effluent stream (i.e., the effluent stream from the oxygen removal reactors).

In various embodiments the effluent stream from the absorber unit comprises oxygen. In various embodiments, the effluent stream from the absorber units has an oxygen content, wherein the oxygen content in the effluent stream from the absorber units is reduced compared to the oxygen content of the effluent stream from the oxygen removal reactors.

In various embodiments the effluent stream from the absorber unit comprises oxygen, wherein the amount of oxygen in the effluent stream (i.e., the oxygen content in the effluent stream) is 1-4,000 parts per million by volume (ppmv). In some embodiments, the effluent stream from the absorber unit comprises oxygen, wherein the amount of oxygen in the effluent stream is 1-2,000 parts per million by volume (ppmv). In some embodiments, the effluent stream from the absorber unit comprises oxygen, wherein the amount of oxygen in the effluent stream is 1-500 parts per million by volume (ppmv).

In some embodiments, the effluent stream from the absorber unit comprises oxygen, wherein the amount of oxygen in the effluent stream is 0, 0-1, 1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-50, 1-60, 1-70, 1-80, 1-90, 1-100, 1-150, 1-200, 1-250, 1-300, 1-350, 1-400, 1-450, 1-500, 1-550, 1-600, 1-650, 1-700, 1-750, 1-800, 1-850, 1-900, 1-950, 1-1000, 1-1050, 1-1100, 1-1150, 1-1200, 1-1250, 1-1300, 1-1350, 1-1400, 1-1450, 1-1500, 1-1550, 1-1600, 1-1650, 1-1700, 1-1750, 1-1800, 1-1850, 1-1900, 1-1950, 1-2000, 1-2050, 1-2100, 1-2150, 1-2200, 1-2250, 1-2300, 1-2350, 1-2400, 1-2450, 1-2500, 1-2550, 1-2600, 1-2650, 1-2700, 1-2750, 1-2800, 1-2850, 1-2900, 1-2950, 1-3000, 1-3050, 1-3100, 1-3150, 1-3200, 1-3250, 1-3300, 1-3350, 1-3400, 1-3450, 1-3500, 1-3550, 1-3600, 1-3650, 1-3700, 1-3750, 1-3800, 1-3850, 1-3900, 1-3950, 1-4000, 1-4050, 1-4100, 1-4150, 1-4200, 1-4250, 1-4300, 1-4350, 1-4400, 1-4450, 1-4500, 1-4550, 1-4500, 1-4550, 1-4600, 1-4650, 1-4600, 1-4650, 1-4700, 1-4750, 1-4800, 1-4850, 1-4900, 1-4950, 1-5000, 1-5050, 1-5100, and 1-5150 parts per million by volume (ppmv).

In some embodiments, the effluent stream from the absorber unit comprises oxygen, wherein the amount of oxygen in the effluent stream is 4000-3950, 4000-3900, 4000-3850, 4000-3800, 4000-3750, 4000-3700, 4000-3650, 4000-3600, 4000-3550, 4000-3500, 4000-3450, 4000-3400, 4000-3350, 4000-3300, 4000-3250, 4000-3200, 4000-3150, 4000-3100, 4000-3050, 4000-3000, 4000-2950, 4000-2900, 4000-2850, 4000-2800, 4000-2750, 4000-2700, 4000-2650, 4000-2600, 4000-2550, 4000-2500, 4000-2450, 4000-2400, 4000-2350, 2350, 4000-2300, 4000-2250, 4000-2200, 4000-2150, 4000-2100, 4000-2050, 4000-2000, 4000-1950, 4000-1900, 4000-1850, 4000-1800, 4000-1750, 4000-1700, 4000-1650, 4000-1600, 4000-1550, 4000-1500, 4000-1450, 4000-1400, 4000-1350, 4000-1300, 4000-1250, 4000-1200, 4000-1150, 4000-1100, 4000-1050, 4000-1000, 4000-950, 4000-900, 4000-850, 4000-800, 4000-750, 4000-700, 4000-650, 4000-600, 4000-550, 4000-500, 4000-450, 4000-400, 4000-350, 4000-300, 4000-250, 4000-200, 4000-150, 4000-100, 4000-90, 4000-80, 4000-70, 4000-60, 4000-50, 4000-40, 4000-30, 4000-20, 4000-10, 4000-9, 4000-8, 4000-7, 4000-6, 4000-5, 4000-4, 4000-3, 4000-2, 4000-1, or 4000-0 parts per million by volume (ppmv).

In various embodiments the effluent stream from the absorber unit comprises oxygen, a ratio of the second oxygen content of the second effluent stream relative to the first oxygen content of the first effluent stream is less than 15%. In some embodiments, a ratio of the second oxygen content of the second effluent stream relative to the first oxygen content of the first effluent stream is less than 10%, that is, the oxygen contained in the product stream can be further removed by the at least one absorber unit. In some embodiments, the ratio of the second oxygen content of the second effluent stream relative to the first oxygen content of the first effluent stream is less than 5%.

In some embodiments, the ratio of the second oxygen content of the second effluent stream relative to the first oxygen content of the first effluent stream is less than 15.0%, less than 14.9%, less than 14.8%, less than 14.7%, less than 14.6%, less than 14.5%, less than 14.4%, less than 14.3%, less than 14.2%, less than 14.1%, less than 14.0%, less than 13.9%, less than 13.8%, less than 13.7%, less than 13.6%, less than 13.5%, less than 13.4%, less than 13.3%, less than 13.2%, less than 13.1%, less than 13.0%, less than 12.9%, less than 12.8%, less than 12.7%, less than 12.6%, less than 12.5%, less than 12.4%, less than 12.3%, less than 12.2%, less than 12.1%, less than 12.0%, less than 11.9%, less than 11.8%, less than 11.7%, less than 11.6%, less than 11.5%, less than 11.4%, less than 11.3%, less than 11.2%, less than 11.1%, less than 11.0%, less than 10.9%, less than 10.8%, less than 10.7%, less than 10.6%, less than 10.5%, less than 10.4%, less than 10.3%, less than 10.2%, less than 10.1%, less than 10.0%, less than 9.9%, less than 9.8%, less than 9.7%, less than 9.6%, less than 9.5%, less than 9.4%, less than 9.3%, less than 9.2%, less than 9.1%, less than 9.0%, less than 8.9%, less than 8.8%, less than 8.7%, less than 8.6%, less than 8.5%, less than 8.4%, less than 8.3%, less than 8.2%, less than 8.1%, less than 8.0%, less than 7.9%, less than 7.8%, less than 7.7%, less than 7.6%, less than 7.5%, less than 7.4%, less than 7.3%, less than 7.2%, less than 7.1%, less than 7.0%, less than 6.9%, less than 6.8%, less than 6.7%, less than 6.6%, less than 6.5%, less than 6.4%, less than 6.3%, less than 6.2%, less than 6.1%, less than 6.0%, less than 5.9%, less than 5.8%, less than 5.7%, less than 5.6%, less than 5.5%, less than 5.4%, less than 5.3%, less than 5.2%, less than 5.1%, less than 5.0%, less than 4.9%, less than 4.8%, less than 4.7%, less than 4.6%, less than 4.5%, less than 4.4%, less than 4.3%, less than 4.2%, less than 4.1%, less than 4.0%, less than 3.9%, less than 3.8%, less than 3.7%, less than 3.6%, less than 3.5%, less than 3.4%, less than 3.3%, less than 3.2%, less than 3.1%, less than 3.0%, less than 2.9%, less than 2.8%, less than 2.7%, less than 2.6%, less than 2.5%, less than 2.4%, less than 2.3%, less than 2.2%, less than 2.1%, less than 2.0%, less than 1.9%, less than 1.8%, less than 1.7%, less than 1.6%, less than 1.5%, less than 1.4%, less than 1.3%, less than 1.2%, less than 1.1%, less than 1.0%, less than 0.9%, less than 0.8%, less than 0.7%, less than 0.6%, or less than 0.5%.

In some embodiments, the ratio of the second oxygen content of the second effluent stream relative to the first oxygen content of the first effluent stream is 15.0% to 0%, 15.0% to 0.1%, 14.9% to 0%, 14.9% to 0.1%, 14.9% to 0.2%, 14.9% to 0.3%, 14.9% to 0.4%, 14.9% to 0.5%, 14.9% to 0.6%, 14.9% to 0.7%, 14.9% to 0.8%, 14.9% to 0.9%, 14.9% to 1.0%, 14.9% to 1.1%, 14.9% to 1.2%, 14.9% to 1.3%, 14.9% to 1.4%, 14.9% to 1.5%, 14.9% to 1.6%, 14.9% to 1.7%, 14.9% to 1.8%, 14.9% to 1.9%, 14.9% to 2.0%, 14.9% to 2.1%, 14.9% to 2.2%, 14.9% to 2.3%, 14.9% to 2.4%, 14.9% to 2.5%, 14.9% to 2.6%, 14.9% to 2.7%, 14.9% to 2.8%, 14.9% to 2.9%, 14.9% to 3.0%, 14.9% to 3.1%, 14.9% to 3.2%, 14.9% to 3.3%, 14.9% to 3.4%, 14.9% to 3.5%, 14.9% to 3.6%, 14.9% to 3.7%, 14.9% to 3.8%, 14.9% to 3.9%, 14.9% to 4.0%, 14.9% to 4.1%, 14.9% to 4.2%, 14.9% to 4.3%, 14.9% to 4.4%, 14.9% to 4.5%, 14.9% to 4.6%, 14.9% to 4.7%, 14.9% to 4.8%, 14.9% to 4.9%, 14.9% to 5.0%, 14.9% to 5.1%, 14.9% to 5.2%, 14.9% to 5.3%, 14.9% to 5.4%, 14.9% to 5.5%, 14.9% to 5.6%, 14.9% to 5.7%, 14.9% to 5.8%, 14.9% to 5.9%, 14.9% to 6.0%, 14.9% to 6.1%, 14.9% to 6.2%, 14.9% to 6.3%, 14.9% to 6.4%, 14.9% to 6.5%, 14.9% to 6.6%, 14.9% to 6.7%, 14.9% to 6.8%, 14.9% to 6.9%, 14.9% to 7.0%, 14.9% to 7.1%, 14.9% to 7.2%, 14.9% to 7.3%, 14.9% to 7.4%, 14.9% to 7.5%, 14.9% to 7.6%, 14.9% to 7.7%, 14.9% to 7.8%, 14.9% to 7.9%, 14.9% to 8.0%, 14.9% to 8.1%, 14.9% to 8.2%, 14.9% to 8.3%, 14.9% to 8.4%, 14.9% to 8.5%, 14.9% to 8.6%, 14.9% to 8.7%, 14.9% to 8.8%, 14.9% to 8.9%, 14.9% to 9.0%, 14.9% to 9.1%, 14.9% to 9.2%, 14.9% to 9.3%, 14.9% to 9.4%, 14.9% to 9.5%, 14.9% to 9.6%, 14.9% to 9.7%, 14.9% to 9.8%, 14.9% to 9.9%, 14.9% to 10.0%, 14.9% to 10.1%, 14.9% to 10.2%, 14.9% to 10.3%, 14.9% to 10.4%, 14.9% to 10.5%, 14.9% to 10.6%, 14.9% to 10.7%, 14.9% to 10.8%, 14.9% to 10.9%, 14.9% to 11.0%, 14.9% to 11.1%, 14.9% to 11.2%, 14.9% to 11.3%, 14.9% to 11.4%, 14.9% to 11.5%, 14.9% to 11.6%, 14.9% to 11.7%, 14.9% to 11.8%, 14.9% to 11.9%, 14.9% to 12.0%, 14.9% to 12.1%, 14.9% to 12.2%, 14.9% to 12.3%, 14.9% to 12.4%, 14.9% to 12.5%, 14.9% to 12.6%, 14.9% to 12.7%, 14.9% to 12.8%, 14.9% to 12.9%, 14.9% to 13.0%, 14.9% to 13.1%, 14.9% to 13.2%, 14.9% to 13.3%, 14.9% to 13.4%, 14.9% to 13.5%, 14.9% to 13.6%, 14.9% to 13.7%, 14.9% to 13.8%, 14.9% to 13.9%, 14.9% to 14.0%, 14.9% to 14.1%, 14.9% to 14.2%, 14.9% to 14.3%, 14.9% to 14.4%, 14.9% to 14.5%, 14.9% to 14.6%, 14.9% to 14.7%, or 14.9% to 14.8%.

In some embodiments, the ratio of the second oxygen content of the second effluent stream relative to the first oxygen content of the first effluent stream is 0.1% to 14.9%, 0.1% to 14.8%, 0.1% to 14.7%, 0.1% to 14.6%, 0.1% to 14.5%, 0.1% to 14.4%, 0.1% to 14.3%, 0.1% to 14.2%, 0.1% to 14.1%, 0.1% to 14.0%, 0.1% to 13.9%, 0.1% to 13.8%, 0.1% to 13.7%, 0.1% to 13.6%, 0.1% to 13.5%, 0.1% to 13.4%, 0.1% to 13.3%, 0.1% to 13.2%, 0.1% to 13.1%, 0.1% to 13.0%, 0.1% to 12.9%, 0.1% to 12.8%, 0.1% to 12.7%, 0.1% to 12.6%, 0.1% to 12.5%, 0.1% to 12.4%, 0.1% to 12.3%, 0.1% to 12.2%, 0.1% to 12.1%, 0.1% to 12.0%, 0.1% to 11.9%, 0.1% to 11.8%, 0.1% to 11.7%, 0.1% to 11.6%, 0.1% to 11.5%, 0.1% to 11.4%, 0.1% to 11.3%, 0.1% to 11.2%, 0.1% to 11.1%, 0.1% to 11.0%, 0.1% to 10.9%, 0.1% to 10.8%, 0.1% to 10.7%, 0.1% to 10.6%, 0.1% to 10.5%, 0.1% to 10.4%, 0.1% to 10.3%, 0.1% to 10.2%, 0.1% to 10.1%, 0.1% to 10.0%, 0.1% to 9.9%, 0.1% to 9.8%, 0.1% to 9.7%, 0.1% to 9.6%, 0.1% to 9.5%, 0.1% to 9.4%, 0.1% to 9.3%, 0.1% to 9.2%, 0.1% to 9.1%, 0.1% to 9.0%, 0.1% to 8.9%, 0.1% to 8.8%, 0.1% to 8.7%, 0.1% to 8.6%, 0.1% to 8.5%, 0.1% to 8.4%, 0.1% to 8.3%, 0.1% to 8.2%, 0.1% to 8.1%, 0.1% to 8.0%, 0.1% to 7.9%, 0.1% to 7.8%, 0.1% to 7.7%, 0.1% to 7.6%, 0.1% to 7.5%, 0.1% to 7.4%, 0.1% to 7.3%, 0.1% to 7.2%, 0.1% to 7.1%, 0.1% to 7.0%, 0.1% to 6.9%, 0.1% to 6.8%, 0.1% to 6.7%, 0.1% to 6.6%, 0.1% to 6.5%, 0.1% to 6.4%, 0.1% to 6.3%, 0.1% to 6.2%, 0.1% to 6.1%, 0.1% to 6.0%, 0.1% to 5.9%, 0.1% to 5.8%, 0.1% to 5.7%, 0.1% to 5.6%, 0.1% to 5.5%, 0.1% to 5.4%, 0.1% to 5.3%, 0.1% to 5.2%, 0.1% to 5.1%, 0.1% to 5.0%, 0.1% to 4.9%, 0.1% to 4.8%, 0.1% to 4.7%, 0.1% to 4.6%, 0.1% to 4.5%, 0.1% to 4.4%, 0.1% to 4.3%, 0.1% to 4.2%, 0.1% to 4.1%, 0.1% to 4.0%, 0.1% to 3.9%, 0.1% to 3.8%, 0.1% to 3.7%, 0.1% to 3.6%, 0.1% to 3.5%, 0.1% to 3.4%, 0.1% to 3.3%, 0.1% to 3.2%, 0.1% to 3.1%, 0.1% to 3.0%, 0.1% to 2.9%, 0.1% to 2.8%, 0.1% to 2.7%, 0.1% to 2.6%, 0.1% to 2.5%, 0.1% to 2.4%, 0.1% to 2.3%, 0.1% to 2.2%, 0.1% to 2.1%, 0.1% to 2.0%, 0.1% to 1.9%, 0.1% to 1.8%, 0.1% to 1.7%, 0.1% to 1.6%, 0.1% to 1.5%, 0.1% to 1.4%, 0.1% to 1.3%, 0.1% to 1.2%, 0.1% to 1.1%, 0.1% to 1.0%, 0.1% to 0.9%, 0.1% to 0.8%, 0.1% to 0.7%, 0.1% to 0.6%, 0.1% to 0.5%, 0.1% to 0.4%, 0.1% to 0.3%, or 0.1% to 0.2%.

In some embodiments, the absorber units and/or oxygen absorbents are at a temperature of 25° C. to 130° C. In some embodiments, the absorber units and/or oxygen absorbents are at a temperature of 25° C. to 100° C. In some embodiments, the absorber units and/or oxygen absorbents are at a temperature of 25° C. to 80° C. In some embodiments, the absorber units are at a temperature of 40° C. to 50° C.

In various embodiments the oxygen removal system of the present invention comprises more than one absorber unit in parallel, allowing oxygen absorbent or an oxygen absorbent bed in one absorber unit to be changed while the other absorber unit is on-line, without shutting down the oxidative dehydrogenation reactor.

In various embodiments, the systems and/or methods of the present invention comprise at least one absorber unit. In various embodiments the systems and/or methods of the present invention comprise at least two absorber units.

In various embodiments, the at least one absorber unit is connected to the cooler. In various embodiments, the at least one absorber unit is connected to and downstream from the cooler.

Oxygen Removal Catalysts

In various embodiments of the present invention, the oxygen removal catalyst comprises at least one metal selected from Fe, Ru, Os, Co, Rh, Ir, Ni, Pd, Pt, and Mn. In various embodiments of the present invention, the oxygen removal catalyst comprises Pd. In other embodiments of the present invention, the oxygen removal catalyst comprises an Mn-based catalyst. In other embodiments of the present invention, the oxygen removal catalyst comprises MnOx. In various embodiments, the oxygen removal catalyst can be supported on a substrate. In various embodiments, the at least one metal can be supported on a substrate. In various embodiments, the oxygen removal catalyst comprises Pd on an $Al_2O_3$ carrier. In various embodiments, the oxygen removal catalyst comprises a mixed oxide of Mn with at least one other metal selected from the group consisting of Cu, Ce, and Al. A non-limiting example of an oxygen removal catalyst is commercially available as BASF R0-20.

In some embodiments, the oxygen removal catalyst is in the form of a catalyst bed.

Oxygen Absorbents

In some embodiments of this disclosure, the effluent from the oxygen removal reactor need not be passed to an oxygen absorbent reactor, but may be cooled and recovered as shown by the apparatus of FIG. 3 and Example 1. In others embodiments of the present invention, the oxygen absorbent comprises at least one metal selected from Cu, Ag, Au, Zn, Cd, and Hg. In various embodiments of the present invention, the oxygen absorbent comprises Cu. In various embodiments, the oxygen absorbent comprises CuO. In various embodiments, the oxygen absorbent comprises CuO and ZnO. Non-limiting examples of an oxygen absorbent are commercially available as PuriStar® R3-16.

In some embodiments, the oxygen absorbent is in the form of an absorbent bed.

Molecular Sieves

In various embodiments of the present invention, the oxygen absorbent comprises a molecular sieve. In some embodiments, the molecular sieve is selected from a type 3A, a type 4A, and any combination thereof. A non-limiting example of a molecular sieve is commercially available as UOP Type-3A.

In some embodiments, the molecular sieve is in the form of a molecular sieve bed.

In various embodiments, the present invention provides a method for removing oxygen from a product stream of an oxidative dehydrogenation process, comprising: contacting the product stream of the oxidative dehydrogenation process with at least one oxygen removal catalyst in at least one oxygen removal reactor under conditions effective to remove at least a portion of the oxygen from the product stream, wherein the product stream has a baseline oxygen content; recovering a first effluent stream from the at least one oxygen removal reactor, wherein the first effluent stream has a first oxygen content, wherein the first oxygen content of the first effluent stream is reduced compared to the baseline oxygen content of the product stream; contacting the first effluent stream with at least one oxygen absorbent in at least one absorber unit under conditions effective to remove at least a portion of the oxygen from the first effluent stream; and recovering a second effluent stream from the at least one absorber unit, wherein the second effluent stream has a second oxygen content, wherein the second oxygen content of the second effluent stream is reduced compared to the first oxygen content of the first effluent stream.

In various embodiments, the present invention provides an oxygen removal system for removing oxygen from a product stream of an oxidative dehydrogenation process, comprising: at least one oxygen removal reactor for preparing a first effluent stream, wherein the at least one oxygen removal reactor comprises at least one oxygen removal catalyst, an inlet for the product stream, and an outlet for the first effluent stream; a supply line for transporting the product stream of the oxidative dehydrogenation process to the at least one oxygen removal reactor, wherein the product stream has a baseline oxygen content; a heater for heating the product stream; a cooler for cooling the first effluent stream; and at least one absorber unit for preparing a second effluent stream, wherein the at least one absorber unit comprises at least one oxygen absorbent, an inlet for the first effluent stream, and an outlet for the second effluent stream; herein the first effluent stream has a first oxygen content, wherein the first oxygen content of the first effluent stream is reduced compared to the baseline oxygen content of the product stream; wherein the second effluent stream has a second oxygen content, wherein the second oxygen content of the second effluent stream is reduced compared to the first oxygen content of the first effluent stream; wherein the heater is connected to the supply line for transporting the product stream to the at least one oxygen removal reactor; wherein the at least one oxygen removal reactor is connected to and downstream from the heater; wherein the cooler is connected to and downstream from the at least one oxygen removal reactor; and wherein the at least one absorber unit is connected to and downstream from the cooler.

In some embodiments, the oxygen removal system further comprises a heat recovery exchanger for optionally heating the product stream by utilizing recoverable heat from the first effluent stream, wherein heat recovery exchanger is: (i) connected to and downstream from the supply line for transporting the product stream of the oxidative dehydrogenation process to the at least one oxygen removal reactor; (ii) connected to and upstream from the heater; (iii) connected to and downstream from the at least one oxygen removal reactor; and (iv) connected to and upstream from the cooler; wherein the at least one oxygen removal reactor is connected to and downstream from the heater; and wherein, the at least one absorber unit is connected to and downstream from the cooler.

Some embodiments of the present invention can be defined as any of the following numbered paragraphs:

1. A method of removing oxygen from an oxygen containing product stream of an oxidative dehydrogenation process, comprising: contacting the product stream of the oxidative dehydrogenation process with at least one oxygen removal catalyst in at least one oxygen removal reactor, wherein the product stream has a baseline oxygen content; and, recovering a first effluent stream from the at least one oxygen removal reactor, wherein the first effluent stream has a first oxygen content, wherein the first oxygen content of the first effluent stream is reduced as compared to the baseline oxygen content of the product stream; wherein the product stream comprises at least two alkenes, at least two alkanes, carbon monoxide, carbon dioxide, water and oxygen; and wherein the at least one oxygen removal catalyst is a Mn-based oxygen removal catalyst.

2. The method of paragraph 1, wherein the contacting step with the Mn-based oxygen removal catalyst is conducted at a first elevated temperature and for a time sufficient to remove at least 72.5% of the baseline oxygen content.

3. The method of paragraph 1, further comprising the step of contacting the first effluent stream with at least one oxygen absorbent in at least one absorber unit at a second elevated temperature after the step of recovering a first effluent stream from the at least one oxygen removal reactor, the second elevated temperature is lower than the first elevated temperature, for a time sufficient to absorb oxygen from said first effluent stream, and recovering a second effluent stream, wherein the second effluent stream has a second oxygen content which is reduced as compared to first oxygen content of the first effluent stream.

4. The method of paragraph 2, wherein the first elevated temperature is in a temperature range of from 150° C.-250° C.

5. The method of paragraph 2, wherein the step of contacting the oxygen containing product stream comprises contacting the product stream with the Mn-based oxygen removal catalyst in the oxygen removal reactor is conducted at a GHSV rate in the range of 4000-9000 $hr^{-1}$.

6. The method of paragraph 3, wherein the second elevated temperature is in the range from 40° C. to 50° C.

7. The method of paragraph 3, wherein the at least one oxygen absorbent comprises at least one metal selected from Cu, Ag, Au, Zn, Cd, and Hg.

8. The method of paragraph 3, wherein the at least one oxygen absorbent comprises a molecular sieve.

9. The method of paragraph 1, wherein the contacting step with the Mn-based catalyst is conducted at a first elevated temperature and for a time sufficient to remove greater than 90% of the baseline oxygen content.

10. The method of paragraph 3, wherein the total oxygen removed from the oxygen containing product stream of the oxidative dehydrogenation process is greater than 96 wt. % after the absorbent step.

11. The method of paragraph 1, wherein the Mn-based catalyst comprises $MnO_x$.

12. The method of paragraph 1, wherein the Mn-based catalyst comprises a mixed oxide of Mn and at least one other metal.

13. The method of paragraph 1, wherein the oxygen containing product stream from the oxidative dehydrogenation process comprises ethylene and propylene, ethane and propane, carbon monoxide, carbon dioxide, water and oxygen.

14. The method of paragraph 13, wherein the oxygen containing product stream from the oxidative dehydrogenation process further comprises methane.

15. The method of paragraph 3, wherein the recovered second effluent stream comprises a reduced amount of carbon monoxide as compared to the carbon monoxide content of the oxygen containing product stream from the oxidative dehydrogenation.
16. The method of paragraph 3, wherein the recovered second effluent stream comprises a water content in an amount in the range of less than or equal to the water content of the oxygen containing product stream from the oxidative dehydrogenation.
17. The method of paragraph 3, wherein the recovered second effluent stream comprises a carbon dioxide content in an amount in the range of less than, equal to, or more than the carbon dioxide content of the oxygen containing product stream from the oxidative dehydrogenation.
18. The method of paragraph 1, wherein the at least two alkanes comprise methane, ethane and propane.
19. The method of paragraph 1, wherein the at least two alkenes comprise ethylene and propylene.
20. The method of paragraph 3, wherein the total oxygen removed from the oxygen containing product stream of the oxidative dehydrogenation process is greater than 99 wt. % after the absorbent step.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

The invention will be further explained by the following examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

A summary of the experimental conditions and results for Example 1 and Comparative Example 1 are provided. The information in Example 1 corresponds to the embodiment in FIG. 3.

As can be seen from Example 1, the oxygen content at the oxygen removal reactor outlet is 452 parts per million volume ("ppmv"), as compared to the oxygen content at the inlet of the oxygen removal reactor which was 5,100 ppmv, a reduction of 91.14%. The catalyst utilized was an Mn-based catalyst, MnOx. Oxygen removal reactor temperature was 250° C. Flow rate through the oxygen removal reactor was 4180 hr$^{-1}$. The other components of the product stream present at the oxygen removal reactor inlet are methane: 15 ppmv, ethylene: 9.17 mol %, ethane: 88.10 mol %, propane: 10 ppmv, propylene: 20 ppmv, carbon monoxide ("CO"): 1.52 mol %, carbon dioxide ("$CO_2$"): 0.58 mol % and water ("$H_2O$"): 0.1 mol %. Other components present at the oxygen removal reactor outlet are CO: 0.59 mol %, $CO_2$: 0.93 mol % and water: 0.1 mol %. Total oxygen removal is calculated at 91.14%.

Comparative Example 1 utilizes a commercially available oxygen removal catalyst available under the trade name of BASF R0-20, available from the BASF corporation.

As can be seen from Comparative Example 1, the oxygen content at the oxygen removal reactor outlet is 620 parts per million volume ("ppmv"), as compared the oxygen removal reactor inlet of 1,107 ppmv, a reduction of 44.00%. Oxygen removal reactor temperature was 150° C. Flow rate through the oxygen removal reactor was 9000 hr$^{-1}$. The other components of the product stream present at the oxygen removal reactor inlet are methane: 62 ppmv, ethylene: 2.91 mol %, ethane: 96.10 mol %, propane: 47 ppmv, propylene: 2 ppmv, carbon monoxide ("CO"): 0.37 mol %, carbon dioxide ("$CO_2$"): 0.26 mol % and water ("$H_2O$"): 0.23 mol %. Other components present at the oxygen removal reactor outlet are CO: 0.26 mol %, $CO_2$: 0.17 mol % and water: 0.23 mol %. Total oxygen removal is calculated at 44.00%.

As can be seen from Example 2, the components present at the oxygen removal reactor outlet of FIG. 3, were cooled by cooler 3 to 40° C. and fed to an inlet 14 of an oxygen absorber unit 4 (FIG. 1) The oxygen absorber unit 4 utilizes a catalyst absorber bed 4a. In Example 2, the catalyst in absorber bed 4a is BASF R3-16. The absorber unit operates at a GHSV of 3000 hr$^{-1}$. The effluent stream leaving absorber unit 4a in Example 2 has the following composition: $O_2$:24 ppmv, CO: 0.59 mol %, $CO_2$: 0.93 mol % and water: 0.1 mol %. Total oxygen removal was 99.53%.

Example 3, demonstrates the results when the product stream composition is altered and Example 4 illustrates the effect when the oxygen removal temperature and GHSV is varied.

In Example 3, the oxygen content at the oxygen removal reactor outlet is 230 parts per million volume ("ppmv"), as compared to the oxygen content at the inlet of the oxygen removal reactor which was 1,107 ppmv, a reduction of 79.22%. The catalyst utilized was an Mn-based catalyst, MnOx. Oxygen removal reactor temperature was 150° C. Flow rate through the oxygen removal reactor was 9000 hr$^-$. The other components of the product stream present at the oxygen removal reactor inlet are methane: 62 ppmv, ethylene: 2.91 mol %, ethane: 96.10 mol %, propane: 47 ppmv, propylene: 2 ppmv, carbon monoxide ("CO"): 0.37 mol %, carbon dioxide ("$CO_2$"): 0.26 mol % and water ("$H_2O$"): 0.23 mol %. Other components present at the oxygen removal reactor outlet are CO: 0.26 mol %, $CO_2$: 0.17 mol % and water: 0.23 mol %. Total oxygen removal is calculated at 79.22%. The components present at the oxygen removal reactor outlet are cooled to 40° C. and then fed to the inlet of an oxygen absorber unit 4 containing BASF R3-16 as an absorbent 4a. GHSV through the absorber unit was 3000 hr$^{-1}$. Absorber unit outlet composition is the following: $O_2$: 31 ppmv, CO: 0.25 mol %, $CO_2$: 0.16 mol %, and water: 0.23 mol %. Total oxygen removal is 97.20%.

Example 4 demonstrates the effect of using a different absorbent in the oxygen removal unit. The oxygen content at the oxygen removal reactor outlet is 412 parts per million volume ("ppmv"), as compared to the oxygen content at the inlet of the oxygen removal reactor which was 1,500 ppmv, a reduction of 72.53%. The catalyst utilized was an Mn-based catalyst, MnOx. Oxygen removal reactor temperature was 165° C. Flow rate through the oxygen removal reactor was 9000 hr$^{-1}$. The other components of the product stream present at the oxygen removal reactor inlet are methane: 65 ppmv, ethylene: 3.76 mol %, ethane: 94.9 mol %, propane: 29 ppmv, propylene: 29 ppmv, carbon monoxide ("CO"): 0.53 mol %, carbon dioxide ("$CO_2$"): 0.40 mol % and water ("$H_2O$"): 0.2 mol %. Other components present at the oxygen removal reactor outlet are CO: 0.38 mol %, $CO_2$: 0.53 mol % and water: 0.2 mol %. Total oxygen removal is calculated at 72.53%. The components present at the oxygen removal reactor outlet are cooled to 40° C. and then fed to the inlet of an oxygen absorber unit 4 containing absorbent UOP 3A, commercially available from Honeywell Corporation as a series 3A molecular sieve. GHSV through the absorber unit was 3000 $hr^{-1}$. Absorber unit outlet composition is the following: $O_2$: 53 ppmv, CO: 0.02 mol %, $CO_2$: 0.14 mol %, and water: 0.01 mol %. Total oxygen removal is 96.47%.

The various methods, systems, and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

A glossary of elements in FIG. 1:
1. Heater
2. Oxygen Removal Reactor
2a. Catalyst Bed
3. Cooler
4. Absorber Unit
4a. Absorbent or Molecular Sieve Bed
6. ODH Product Stream
7. Supply Line
I1. Heater Inlet
I2. Oxygen Removal Reactor Inlet
I3. Cooler Inlet
I4. Absorber Unit Inlet
O1. Absorber Unit Outlet A glossary of elements in FIG. 2:
1. Heater
2. Oxygen Removal Reactor
2a. Catalyst Bed
3. Cooler
4. Absorber Unit
4a. Absorbent or Molecular Sieve Bed 5. Heat Recovery Exchanger
6. ODH Product Stream
7. Supply Line
I1. Heater Inlet
I2. Oxygen Removal Reactor Inlet
I3. Cooler Inlet
I4. Absorber Unit Inlet
O1. Absorber Unit Outlet A glossary of elements in FIG. 3:
1. Heater
2. Oxygen Removal Reactor
2a. Catalyst Bed
3. Cooler
6. ODH Product Stream
7. Supply Line
I1. Heater inlet
I2. Oxygen Removal Reactor Inlet
I3. Cooler Inlet
O2. Cooler Outlet

What is claimed is:

1. A method of removing oxygen from an oxygen containing product stream of an oxidative dehydrogenation process, comprising:
contacting the product stream of the oxidative dehydrogenation process with at least one oxygen removal catalyst in at least one oxygen removal reactor at a first elevated temperature; wherein the product stream has a baseline oxygen content; and,
recovering a first effluent stream from the at least one oxygen removal reactor, wherein the first effluent stream has a first oxygen content, wherein the first oxygen content of the first effluent stream is reduced as compared to the baseline oxygen content of the product stream;
cooling the first effluent to a temperature in the range of 25° C. to 50° C. before contacting the first effluent stream with at least one oxygen absorbent in at least one oxygen absorber; and
contacting the cooled first effluent stream with the at least one oxygen absorbent in the at least one oxygen absorber unit in the absence of added unreacted (free) hydrogen at a second elevated temperature for a time sufficient to absorb oxygen from said first effluent stream, wherein said second elevated temperature is lower than the first elevated temperature, and recovering a second effluent stream, wherein the second effluent stream has a second oxygen content which is reduced as compared to first oxygen content of the first effluent stream;
wherein the product stream comprises at least two alkenes, at least two alkanes, carbon monoxide, carbon dioxide, water and oxygen;
wherein the at least one oxygen removal catalyst is a Mn-based oxygen removal catalyst; and
wherein the at least one oxygen absorbent comprises at least one metal selected from the group consisting of Cu, Ag, Au, Zn, Cd, and Hg.

2. The method of claim 1, wherein the contacting step with the Mn-based oxygen removal catalyst is conducted at a first elevated temperature and for a time sufficient to remove at least 72.5% of the baseline oxygen content.

3. The method of claim 2, wherein the first elevated temperature is in a temperature range of from 150° C.-250° C.

4. The method of claim 2, wherein the step of contacting the oxygen containing product stream comprises contacting the product stream with the Mn-based oxygen removal catalyst in the oxygen removal reactor is conducted at a GHSV rate in the range of 4000-9000 $hr^{-1}$.

5. The method of claim 1, wherein the at least one oxygen absorbent comprises a molecular sieve.

6. The method of claim 1, wherein the contacting step with the Mn-based catalyst is conducted at a first elevated temperature and for a time sufficient to remove greater than 90% of the baseline oxygen content.

7. The method of claim 1, wherein the total oxygen removed from the oxygen containing product stream of the oxidative dehydrogenation process is greater than 96 wt. % after the absorbent step.

8. The method of claim 1, wherein the Mn-based catalyst comprises $MnO_x$.

9. The method of claim 1, wherein the Mn-based catalyst comprises a mixed oxide of Mn and at least one other metal.

10. The method of claim 1, wherein the oxygen containing product stream from the oxidative dehydrogenation process comprises ethylene and propylene, ethane and propane, carbon monoxide, carbon dioxide, water and oxygen.

11. The method of claim 10, wherein the oxygen containing product stream from the oxidative dehydrogenation process further comprises methane.

12. The method of claim 1, wherein the recovered second effluent stream comprises a reduced amount of carbon monoxide as compared to the carbon monoxide content of the oxygen containing product stream from the oxidative dehydrogenation.

13. The method of claim 1, wherein the recovered second effluent stream comprises a water content in an amount in the range of less than or equal to the water content of the oxygen containing product stream from the oxidative dehydrogenation.

14. The method of claim 1, wherein the recovered second effluent stream comprises a carbon dioxide content in an amount in the range of less than, equal to, or more than the carbon dioxide content of the oxygen containing product stream from the oxidative dehydrogenation.

15. The method of claim 1, wherein the at least two alkanes comprise methane, ethane and propane.

16. The method of claim 1, wherein the at least two alkenes comprise ethylene and propylene.

17. The method of claim 1, wherein the total oxygen removed from the oxygen containing product stream of the oxidative dehydrogenation process is greater than 99 wt. % after the absorbent step.

18. The method of claim 2, wherein the step of contacting the oxygen containing product stream comprises contacting the product stream with the Mn-based oxygen removal catalyst in the oxygen removal reactor is conducted at a GHSV rate in the range of 4180-9000 $hr^{-1}$.

19. The method of claim 1, wherein the at least one oxygen absorbent comprises at least one metal selected from Cu and Zn.

* * * * *